United States Patent

Kelly et al.

[11] Patent Number: 6,162,831
[45] Date of Patent: Dec. 19, 2000

[54] MEDICAL TREATMENT TO LOWER URIC ACID LEVELS

[75] Inventors: Peter Finian Kelly; Stephen Paul Jones, both of Nottinghamshire, United Kingdom

[73] Assignee: Knoll Aktiengesellschaft, Ludwigshafen, Germany

[21] Appl. No.: 09/269,339

[22] PCT Filed: Sep. 15, 1997

[86] PCT No.: PCT/EP97/05034

§ 371 Date: Mar. 25, 1999

§ 102(e) Date: Mar. 25, 1999

[87] PCT Pub. No.: WO98/13033

PCT Pub. Date: Apr. 2, 1998

[30] Foreign Application Priority Data

Sep. 25, 1996 [GB] United Kingdom .................... 9619962

[51] Int. Cl.⁷ .................................................. A61K 31/135
[52] U.S. Cl. .............................................................. 514/646
[58] Field of Search ............................................. 514/646

[56] References Cited

U.S. PATENT DOCUMENTS 4,939,175  7/1990  Ukai et al. ............................. 514/646

FOREIGN PATENT DOCUMENTS

| | | |
|---|---|---|
| 230742 | 8/1987 | European Pat. Off. . |
| 282206 | 9/1988 | European Pat. Off. . |
| 339280 | 11/1989 | European Pat. Off. . |
| 2098602 | 11/1982 | United Kingdom . |
| 90/06110 | 6/1990 | WIPO . |
| 94/00047 | 1/1994 | WIPO . |
| 94/00114 | 1/1994 | WIPO . |
| 95/20949 | 8/1995 | WIPO . |

*Primary Examiner*—Kimberly Jordan
*Attorney, Agent, or Firm*—Keil & Weinkauf

[57] ABSTRACT

A compound of formula I

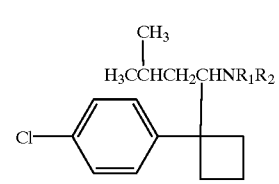

or a pharmaceutically acceptable salt thereof in which $R_1$ and $R_2$ are independently H or methyl (for example N,N-dimethyl-1-[1-(4-chlorophenyl)cyclobutyl]-3-methylbutyl amine hydrochloride optionally in the form of its monohydrate) is used for lowering the uric acid level in humans, for example in humans suffering from or at risk of developing gout, hyperuricaemia or coronary heart disease.

5 Claims, No Drawings

MEDICAL TREATMENT TO LOWER URIC ACID LEVELS

This application is a 371 of PCT/EP97/05034, filed Sep. 15, 1997.

This invention relates to a method of lowering uric acid levels in the human body.

According to the present invention there is provided a method of lowering the uric acid level in the human body comprising administering to a human in need thereof a therapeutically effective amount of a compound of formula I

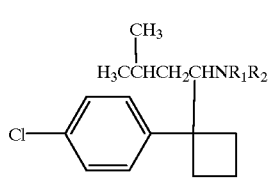

including enantiomers and pharmaceutically acceptable salts thereof, in which $R_1$ and $R_2$ are independently H or methyl, in conjunction with a pharmaceutically acceptable diluent or carrier.

The preparation and use of compounds of formula I, such as N,N-dimethyl-1-[1-(4-chlorophenyl)cyclobutyl]-3-methylbutylamine (or N-{1-[1-(4-chlorophenyl) cyclobutyl]-3-methylbutyl}-N,N-dimethylamine) and salts thereof, in the treatment of depression is described in British Patent Specification 2098602. The use of compounds of formula I such as N,N-dimethyl-1-[1-(4-chlorophenyl) cyclobutyl]-3-methylbutylamine and salts thereof in the treatment of Parkinson's disease is described in European Patent Number 282206. The use of N,N-dimethyl-1-[1-(4-chlorophenyl)cyclobutyl]-3-methylbutylamine and salts thereof in the treatment of cerebral function disorders is described in U.S. Pat. No. 4939175. The use of N,N-dimethyl-1-[1-(4-chlorophenyl)cyclobutyl]-3-methylbutylamine hydrochloride in the treatment of obesity is described in European Patent Number 397831. A particularly preferred form of this compound is N,N-dimethyl-1-[1-(4-chlorophenyl)cyclobutyl]-3-methylbutylamine hydrochloride monohydrate (sibutramine hydrochloride monohydrate) which is described in European Patent Number 230742. The use of N,N-dimethyl-1-[1-(4-chlorophenyl) cyclobutyl]-3-methylbutylamine and salts thereof for improving the glucose tolerance of humans having Impaired Glucose Tolerance or Non-insulin Dependent Diabetes Mellitus is described in published PCT application WO95/20949.

It may be appreciated by those skilled in the art that compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

It will be appreciated by those skilled in the art that compounds of formula I contain a chiral centre. When a compound of formula I contains a single chiral centre it may exist in two enantiomeric forms. The present invention includes the use of the individual enantiomers and mixtures of the enantiomers. The enantiomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer to the other by asymmetric transformation.

Surprisingly, it has now been found that compounds of formula I have the ability to lower the uric acid level in the human body, and therefore have utility as uric acid-lowering agents. The presence of this activity indicates that compounds of formula I have use in the treatment and prophylaxis of conditions in which there is an elevated uric acid level, for example hyperuricaemia and gout. The compounds may also have utility in lowering the uric acid level in humans having or at risk of developing coronary heart disease.

Preferably, the present invention provides a method for the treatment and/or prophylaxis of gout or hyperuricaemia comprising the administration of a therapeutically effective amount of a compound of formula I in conjunction with a pharmaceutically acceptable diluent or carrier to a human in need thereof.

The present invention further comprises the use of a compound of formula I

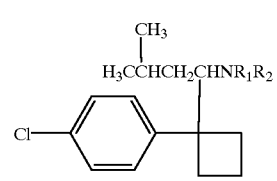

including enantiomers and pharmaceutically acceptable salts thereof, in which $R_1$ and $R_2$ are independently H or methyl, in the manufacture of a medicament for lowering the uric acid level in humans, for example in humans suffering from or at increased risk of developing gout, hyperuricaemia or coronary heart disease. Preferably, the medicament is used in the treatment and/or prophylaxis of conditions in which there is an elevated uric acid level, for example hyperuricaemia or gout. The compounds may also have utility in lowering the uric acid level in humans having or at risk of developing coronary heart disease.

Specific compounds of formula I are N,N-dimethyl-1-[1-(4-chlorophenyl)cyclobutyl]-3-methylbutylamine, N-{1-[1-(4-chlorophenyl)cyclobutyl]-3-methylbutyl}-N-methylamine, and 1-[1-(4-chlorophenyl)cyclobutyl]-3-methylbutylamine including racemates, individual enantiomers and mixtures thereof, and pharmaceutically acceptable salts thereof. A preferred compound of formula I is N,N-dimethyl-1-[1-(4-chlorophenyl)cyclobutyl]-3-methylbutylamine or a salt thereof, for example the hydrochloride salt. A preferred form of this hydrochloride is its monohydrate.

The compound of formula I may be administered in any of the known pharmaceutical dosage forms. The amount of the compound to be administered will depend on a number of factors including the age of the patient, the severity of the condition and the past medical history of the patient and always lies within the sound discretion of the administering physician but it is generally envisaged that the dosage of the compound to be administered will be in the range 0.1 to 50 mg preferably 1 to 30 mg per day given in one or more doses.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacist's art. Tablets may be prepared from a mixture of the active compound with fillers, for example calcium phosphate; disintegrating agents, for example maize starch; lubricating agents, for example magnesium stearate; binders, for example microcrystalline cellulose or polyvinylpyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 1 to 50 mg of the active compound.

Other dosage forms for oral administration include, for example, aqueous suspensions containing the active compound in an aqueous medium in the presence of a non-toxic suspending agent such as sodium carboxy-methylcellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, eg an effervescent couple formed from an acid and a carbonate or bicarbonate salt to facilitate dispersion in the liquid medium.

The therapeutically active compounds of formula I may be formulated into a composition which the patient retains in his mouth so that the active compound is administered through the mucosa of the mouth.

Dosage forms suitable for rectal administration are the known pharmaceutical forms for such administration, for example, suppositories with cocoa butter or polyethylene glycol bases.

Dosage forms suitable for parenteral administration are the known pharmaceutical forms for such administration, for example sterile suspensions or sterile solutions in a suitable solvent.

Dosage forms for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The therapeutically active compound of formula I may be formulated into a composition which is dispersed as an aerosol into the patients oral or nasal cavity. Such aerosols may be administered from a pump pack or from a pressurised pack containing a volatile propellant.

The therapeutically active compounds of formula I used in the method of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as an oily suspension of the compound to be infused for example in the form of a very sparingly water-soluble derivative such as a dodecanoate salt or a lipophilic ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

In another aspect, the invention provides a pharmaceutical composition for lowering the uric acid level in the human body, for example in humans suffering from or at increased risk of developing gout or hyperuricaemia, comprising a compound of formula I

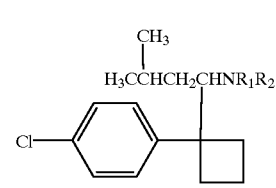

I including enantiomers and pharmaceutically acceptable salts thereof, in which $R_1$ and $R_2$ are independently H or methyl, in conjunction with a pharmaceutically acceptable diluent or carrier.

The efficacy of compounds of formula I in lowering plasma uric acid levels has been demonstrated in clinical trials as follows. It will be appreciated that a 10 mg dose or a 15 mg dose of sibutramine in the form of the hydrochloride monohydrate is equivalent to 8.37 mg or 12.55 mg of sibutramine as free base respectively.

Trial 1

In a clinically supervised trial, 485 mild to moderately obese patients were randomised to receive placebo, sibutramine hydrochloride monohydrate (10 mg) or sibutramine hydrochloride monohydrate (15 mg) orally once daily for 12 months. Reductions in uric acid levels were observed at month 6, and were maintained at month 12; the decreases in the sibutramine groups were greater than in the placebo group. The differences were statistically significant for the difference between sibutramine hydrochloride monohydrate 10 mg and placebo at month 6 and for the difference between sibutramine hydrochloride monohydrate 15 mg and placebo at month 6, endpoint and final assessment. The difference between sibutramine hydrochloride monohydrate 15 mg and 10 mg was also statistically significant at the final assessment ($p<0.05$). The data were analysed retrospectively according to weight loss.

Serum Uric Acid—Summary of Mean Percentage Change From Baseline to Endpoint for Long-term Study (LOCF)

| Sub-group | Placebo | Sibutramine (10 mg) | Sibutramine (15 mg) |
|---|---|---|---|
| All patients | −1.7 | −5.6* | −7.8** |
| ≧5% weight loss | −3.9 | −9.5*** | −10.0*** |
| ≧10% weight loss | −4.7 | −14.1*** | −11.1*** |

'Sibutramine' and 'sib' mean sibutramine hydrochloride monohydrate
Baseline values ($\mu$mol/l):
Placebo 312.8; sib 10 mg 310.7; sib 15 mg 307.4
*p ≦ 0.05 vs. all placebo
**p ≦ 0.01 vs. all placebo
***p ≦ 0.001 vs. all placebo Trial 2

In a further clinically supervised trial, 160 obese patients following a very low calorie diet were randomised to receive placebo or sibutramine hydrochloride monohydrate (10 mg) orally once daily for 12 months. Statistically significant reductions in uric acid levels were observed in the sibutramine group at month 6 and endpoint compared to placebo. The data were analysed retrospectively according to weight loss.

Serum Uric Acid—Summary of Mean Percentage Change From Baseline to End-point for Long-term Study (LOCF)

| Sub-group | Placebo | Sibutramine (10 mg) |
|---|---|---|
| All patients | −11.1 | −19.0** |
| ≧5% weight loss | −22.5 | −21.7* |
| ≧10% weight loss | −28.2 | −27.1*** |

'Sibutramine' means sibutramine hydrochloride monohydrate
Baseline values ($\mu$mol/l):
Placebo 328.5; sibutramine 10 mg 335.4
*p ≦ 0.05 vs. all placebo
**p ≦ 0.01 vs. all placebo
***p ≦ 0.001 vs. all placebo The above results support the utility of compounds of formula I in lowering uric acid levels.

What is claimed is:

1. A method of lowering the uric acid level in the human body comprising administering to a human in need thereof a therapeutically effective amount of a compound of formula I

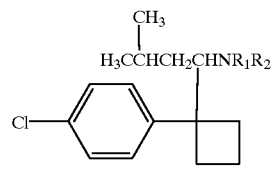

including enantiomers and pharmaceutically acceptable salts thereof in which $R_1$ and $R_2$ are independently H or methyl, in conjunction with a pharmaceutically acceptable diluent or carrier.

2. A method as claimed in claim 1 in which the human is suffering from gout or hyperuricaemia.

3. A method as claimed in claim 1 wherein the compound of formula I is N,N-dimethyl-1-[1-(4-chlorophenyl) cyclobutyl]-3-methylbutylamine hydrochloride.

4. A method as claimed in claim 1 wherein the compound of formula I is N,N-dimethyl-1-[1-(4-chlorophenyl) cyclobutyl]-3-methylbutylamine hydrochloride in the form of its monohydrate.

5. A method of prophylaxis of gout, hyperuricaemia or coronary heart disease in humans at increased risk of developing these conditions, comprising the administration of a therapeutically effective amount of a compound of formula I, as defined in claim 1, in conjunction with a pharmaceutically acceptable diluent or carrier to a human in need thereof.

* * * * *